United States Patent [19]

Brownlee

[11] Patent Number: 5,630,835
[45] Date of Patent: May 20, 1997

[54] METHOD AND APPARATUS FOR THE SUPPRESSION OF FAR-FIELD INTERFERENCE SIGNALS FOR IMPLANTABLE DEVICE DATA TRANSMISSION SYSTEMS

[75] Inventor: Robert R. Brownlee, Ormond Beach, Fla.

[73] Assignee: Cardiac Control Systems, Inc., Palm Coast, Fla.

[21] Appl. No.: 506,302

[22] Filed: Jul. 24, 1995

[51] Int. Cl.⁶ ............................................. A61N 1/37
[52] U.S. Cl. ........................... 607/60; 128/903; 607/32
[58] Field of Search ............................. 128/903; 607/32, 607/60

[56] References Cited

U.S. PATENT DOCUMENTS

| | | | |
|---|---|---|---|
| 3,990,030 | 11/1976 | Chamberlin | 336/65 |
| 4,038,990 | 8/1977 | Thompson | 128/419 |
| 4,494,545 | 1/1985 | Slocum et al. | 607/32 |
| 4,539,992 | 9/1985 | Calfee et al. | 128/419 |
| 4,562,840 | 1/1986 | Batina et al. | 128/419 |
| 4,586,508 | 5/1986 | Batina et al. | 607/32 |
| 4,944,299 | 7/1990 | Silvian | 128/419 |
| 5,107,833 | 4/1992 | Barsness | 128/419 |
| 5,117,825 | 6/1992 | Grevious | 128/419 |
| 5,168,871 | 12/1992 | Grevious | 128/419 |
| 5,391,194 | 2/1995 | Goldreyer | 607/31 |

*Primary Examiner*—William E. Kamm
*Attorney, Agent, or Firm*—Kerkam, Stowell, Kondracki & Clarke; Dennis P. Clarke

[57] ABSTRACT

An electronic device for non-invasively communicating with an implanted device, such as, for example, a cardiac pacemaker. The electronic programming device includes a transceiver having an antenna, a transmitter portion and a receiver portion. The antenna portion is arranged to have two coils arranged in series phase opposition to suppress the effects of far-field interference signals on received near-field signals from the implanted device, when the transceiver is receiving data from the implanted device. The electronic device further includes means to isolate the transmit and receive functions thereof to prevent cancellation of the transmitted signal when the transceiver is in the transmit mode.

26 Claims, 4 Drawing Sheets

METHOD AND APPARATUS FOR THE SUPPRESSION OF FAR-FIELD INTERFERENCE SIGNALS FOR IMPLANTABLE DEVICE DATA TRANSMISSION SYSTEMS

FIELD OF THE INVENTION

The present invention relates to a method and apparatus for suppressing far-field interference signals in an implantable device data link. In particular, the method and apparatus facilitate far-field interference signal suppression while allowing and facilitating the detection of desirable near-field data signals from the implanted device.

BACKGROUND OF THE INVENTION

As implantable medical devices, in general, and cardiac pacers, in particular, have become more complex in operation, it has also become desirable to non-invasively transfer data both to and from the implantable device and an external device. The transfer of signals from the external device to the implanted device to modify the operating parameters thereof is referred to in the art as programming. Data is also transferred from the implanted device to the external device to provide various monitoring information. These transfers of signals and data to and from the implanted devices is referred to as telemetry.

In the field of programmable implanted medical devices, such as, for example, cardiac pacemakers, tachyarrhythmia control devices, implantable drug dispensers, nerve simulators, and the like, it has become common to provide an interactive transceiver system for both remotely programming operating functions, modes and parameters of the implanted device and receiving data from the device related thereto on command using radio-frequency telemetry systems. In nearly all such active electronic implanted devices, it has become highly desirable to have the ability to reprogram the device's modes of operation, parameters and other functions, and to monitor the performance thereof, both historically and contemporaneously. Such implanted electronic devices are designed to provide two-way telemetry by radio frequency signal transmission and reception between the implanted device and an antenna disposed in a programming head or wand of the external programming device to provide for the exchange of transmitted information, thereby enabling the aforementioned programming by telemetry-in and the reading out of data stored in the device by telemetry-out. The transmission of signals has generally been accomplished using a single coil antenna on the external device to transmit and receive signals to and from a single coil internal antenna of the implanted device.

Because the implanted device is usually powered by a primary cell, it is important to limit the energy consumption and current drain required for data transmission in order to conserve the cell's energy for use in its intended work function, i.e., in the case of a cardiac pacer, stimulating and sensing cardiac muscle. Thus, the current state of the art is to transfer signals between the implanted device and the external programmer using a radio frequency carrier employing very close spacing of the transmitting and receiving antennae. Such close spacing provides low-power operation for a given minimum signal-to-noise ratio in accordance with the well-known inverse square law.

The maximum required data transmission distance in such systems is on the order of two to three inches. This limitation of the required transmission distance allows containment of the transmission power to a few microwatts from the primary cell of the implanted device. Additionally, in the low-power data link described, the external receiver system must be of a very high gain. The high-gain requirement renders such systems vulnerable to noise generated by extraneous fields, generated by myriad interfering sources found in the modern electric- and magnetic-field environment. All forms of electronic systems, such as, for example, computers, printers, cathode ray viewing tubes and lighting control systems, are potential interfering sources to implant data transmission systems.

If an extraneous field has energy components in the pass band of the system employed to receive data from the weak field emanating from the implant, and if the extraneous field strength is in the range transmitted from the implant, it is very difficult to mitigate the interfering effect on the data link. Many prior art systems have attempted to overcome the adverse effects of noise created by extraneous fields by increasing the gain of the antennae of the telemetry system. This solution has many drawbacks, including increased power consumption. Furthermore, these prior systems do nothing to mitigate the effect of the extraneous fields, they merely attempt to overpower the noise.

SUMMARY OF THE INVENTION

The present invention provides a method and apparatus that overcomes the deficiencies of known implantable device data transmission systems, especially with respect to mitigating the deleterious effects of interference signals generated by far-field sources in such systems. In particular, the present invention provides a method and apparatus to suppress far-field interference signals in an implantable device data link by employing two external receiver coils connected in serial phase opposition and separated spatially so as to effect suppression of far-field interference signals, while allowing the detection of near-field data signals from the implanted device.

It is, therefore, an object of the invention to suppress far-field interference signals in implantable device data link systems when detecting near-field signals emanating from the implanted device.

It is another object of the present invention to provide the ability to isolate the transmit and receive modes of the external transceiver. Isolation may be accomplished by disabling the far-field interference signal suppression arrangement when transmitting data from an external transceiver to the implanted device.

It is still another object of the present invention to provide a means to automatically disable the suppression arrangement when the transmission energy of the external transceiver exceeds a predetermined level.

In another embodiment of the present invention, signals received by the respective coils of the transceiver are transmitted to an active circuit which processes the received signals to mitigate the effect of the far-field interference signals, when the transceiver is in a receive mode. In this embodiment, only one of the coils is connected to the transmitter of the transceiver, thereby providing isolation between the receive and transmit modes of the transceiver, and, thus, obviating the need for a disabling arrangement for disabling one of the coils during transmission of data from the transceiver to the implanted device.

These and other objects, and their attendant advantages, are achieved by the present invention, which provides an electronic device for non-invasive communication with an implanted electronic device, comprising: a transceiver, including an antenna, a transmitter portion and a receiver portion, said transceiver being able to send data to and receive data from said implanted device; said antenna comprising first and second coils arranged in series phase opposition to suppress far-field interference signals when said transceiver is receiving data from said implanted device; and further including an isolation circuit for isolating the transmit and receive modes of the transceiver by using a disabling circuit to disable said second coil when said transceiver is transmitting data to the implanted device.

The present invention also provides a method for suppressing far-field interference signals when non-invasively communicating with an implanted electronic device using an external transceiver, comprising the steps of: receiving a signal from the implanted device via an antenna of the transceiver, said antenna comprising first and second coils, said first and second coils being spatially separated and arranged in serial phase opposition; subtracting signals received on the respective first and second coils to obtain a resultant signal, said resultant signal being representative of data received from said implanted device; and transmitting said resultant signal to a receiver portion of the transceiver.

BRIEF DESCRIPTION OF THE DRAWINGS

The invention will be described in detail herein with reference to the following drawings in which like reference numerals refer to like elements throughout the several views, and wherein.

DETAILED DESCRIPTION OF PREFERRED EMBODIMENTS

Figure 1:
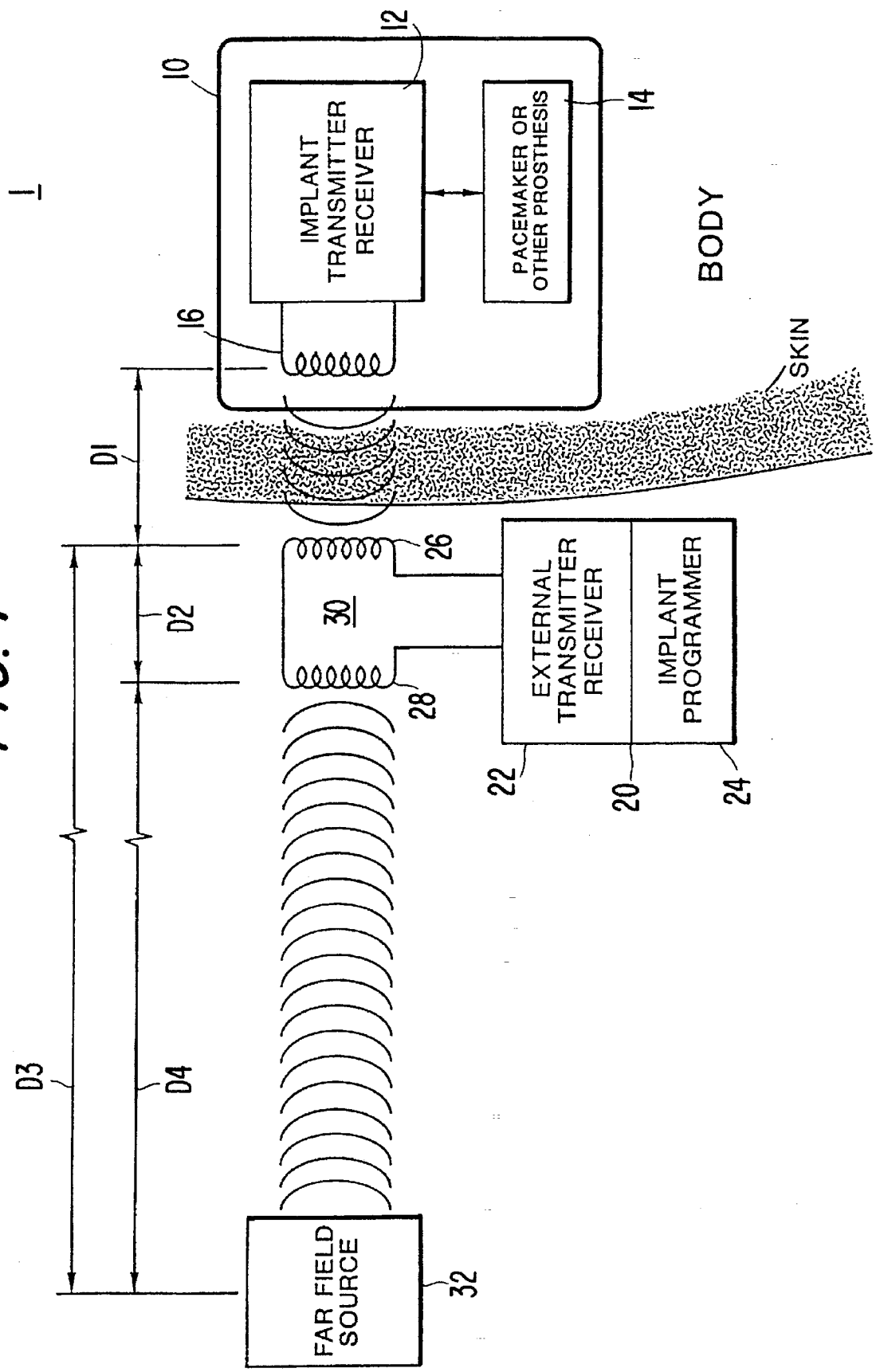
FIG. 1 is a schematic illustration of a system for non-invasive communication with an implanted device, in accordance with an embodiment of the present invention.

Referring to FIG. 1, a schematic illustration of the far-field suppression device according to the present invention is shown. The system 1 includes an internal device 10 and an external communication device 20. The internal device 10 includes an implant transceiver 12 coupled to an internal coil 16. The implant transceiver 12 communicates signals received from the internal coil 16 to the implanted medical device 14. The implanted device 14 may be any of a number of various devices that are implantable within the body of a living organism, such as, for example, human beings. Examples of implanted devices 14, include, but are not limited to, cardiac pacemakers, tachyarrhythmia control devices, implantable drug dispensers, nerve simulators, and the like. For illustrative convenience, the implanted device 14 may be alternatively referred to as a cardiac pacemaker.

The external device 20 includes a transceiver 22 coupled, on one end, to an antenna arrangement 30, and on the other end to an implant programmer 24, or the like. Modern implantable devices 10 are non-invasively programmable via an external coupling coil that transmits data transcutaneously to a receiver coil contained within the implant. Usually the data link is a two-way transmission system requiring that the implantable device also be capable of transmitting data from the implant transcutaneously to the external receiver coil on command. In prior art systems, the antenna arrangement of the external transceiver generally included only one coil for transmitting and receiving data to and from the internal device 10 via the internal coil 16. The maximum required data transmission distance of these systems is on the order of two to three inches. Due to the relatively short distances associated with the near-field transmission between the implanted device and the external device, and the desire of designers to conserve power drain associated with the primary cell of the implanted device, the external receiver system conventionally required very high-gain levels.

However, the high-gain requirement renders the system vulnerable to interference from far-field electronic noise generating devices. These electronic noise-generating devices include almost all electronic devices commonly found in the modern hospital environment, including, for example, computers, printers, cathode-ray viewing tubes, lighting systems, and the like. If an external field generated by an electronic device has energy components within the pass band of the system employed to receive data from the relatively weak near-field emanating from the implant, and if the extraneous field strength is in the range transmitted from the implant, it is very difficult to mitigate the interfering effect of such extraneous fields on the data link.

To alleviate the detrimental effect far-field interference signals may have on such a system, the present invention incorporates a new antenna arrangement 30, which, as described herein, minimizes the effects of far-field interference signals on the system when the external device 20 is receiving data from the internal device 10. Specifically, the antenna arrangement 30 includes, not one, but two coils 26, 28 connected to the transceiver 22 of the external device. The coils 26, 28 are arranged in series phase opposition, whereby the signals received on each of the coils are subtracted, thereby eliminating a major component of the far-field interference signal.

A brief overview of the behavior of near- and far-fields in the intended environment will be instructive. A change in the location of the receiver coil at the near-field observation site effects a major difference in sensing near- and far-field sources even within the same frequency band. Attenuation of field strength with distance from the transmitting source follows an inverse square law function, such that the near-field signal strength changes dramatically with changes in distance from the emanating near-field source. In contrast, the far-field signal strength remains nearly unchanged with an equal change in distance from the source because the effective distance change, i.e., the ratio of the first distance to the second distance, relative to the far-field distance is negligible. For example, assume that an external receiver coil is initially placed a distance of one inch from an implant transmission coil and ten feet from a far-field interfering source. If the external receiver coil were moved one inch further from the implant transmission coil, the near-field signal strength and resultant coil output would be reduced by a factor of four, i.e. $1/D^2=\frac{1}{2}^2=\frac{1}{4}$. Considering the far-field source, an identical change in distance of one inch is seen in context with a reference distance of 120 inches (ten feet). The resultant signal strength of the far-field interfering signal would be diminished by a factor of only about 0.02.

This disparity in signal strength with changes in distance from the near- and far-field sites can be advantageously exploited by employing two receiver coils 26, 28 and connecting them in phase opposition as shown in FIG. 1. Referring to FIG. 1, assume that at coil site 26 the field strength from both the near-field and far-field sources are identical and equal to a normalized value of one (1), thereby creating an interference situation. Further assume that the distance D1 between coil site 26 and internal coil site 16 is one inch, and the distance D2 between coil site 26 and coil site 28 is also one inch. Also assume that the far-field interfering source 32 is located at a distance D3 from coil site 26 of 120 inches and at a distance D4 from coil site 28 of 119 inches. Using the inverse square relationship, $1/D^2$, the near-field level at coil site 28 would be ¼ that at coil site 26. This would render a normalized output of 0.75 with the distance doubled and with the signals from the two coils 26, 28 subtracted by virtue of being connected in phase opposition. It should be noted that phase opposition can only be assured if the wavelengths of the source fields are long compared to the coil separation distance.

Considering now the far-field case, the source level at the far-field site 32 would have to be $1 \times D^2$ to provide equal magnitudes of near-field and far-field levels at coil site 26. The relative level at the far-field source 32 would have to be $1 \times (120")^2$ to satisfy this requirement. The level at coil site 28 can then be calculated from the derived source level and the distance from coil site 28 of the far-field source 32. This distance is 119 inches. Thus, the level at coils site 28 is calculated by dividing the relative source level of $(120")^2$ by $(119")^2$. The normalized far-field level at coil site 28 then calculates to 1.016.

Subtraction of the far-field signals developed in coils 26, 28 provides a resultant of 0.016. Comparing this combined far-field level to the near-field combined resultant level of 0.75 derived earlier highlights the dramatic improvement in the signal-to-noise ratio of the arrangement of the present invention as compared to the single coil case. Using only one external coil, the signal-to-noise ratio is 1/1, but with the use of two oppositely-phased coils 26, 28, the ratio is 0.75/0.016, or in the order of 47/1, thus rendering the extraneous signal harmless to the data transmission link. It should also be noted that cancellation of the near-field signal can occur if the phase-opposed coils 26, 28 do not have adequate spatial separation. Thus, it is important to ensure that there is adequate spatial separation between the coils 26, 28 to prevent cancellation of the near-field signal. It has been found that a spatial separation in the range of 0.25 to 1.00 inches is preferable in the case of implanted cardiac pacemakers.

When transmitting data from the external device 20 to the internal device 10, the simple series phase-opposed coil arrangement 30 shown in FIG. 1 would be detrimental. In the case of transmission, both coils 26, 28 act essentially as closely coupled near-field sources. This arrangement would lead to cancellation of the transmitted energy, thus rendering the system ineffective for transmission of data from the external device 20 to the internal device 10. Therefore, in the practical case, it would be preferable to isolate the transmit and receive functions electronically, thereby permitting the use of the same set of coils for both the transmit in and out directions. There are several equally acceptable ways to isolate the transmit and receive functions electronically. Three exemplary and preferred alternatives are illustrated and will be discussed with reference to FIGS. 2-4.

Figure 2A:
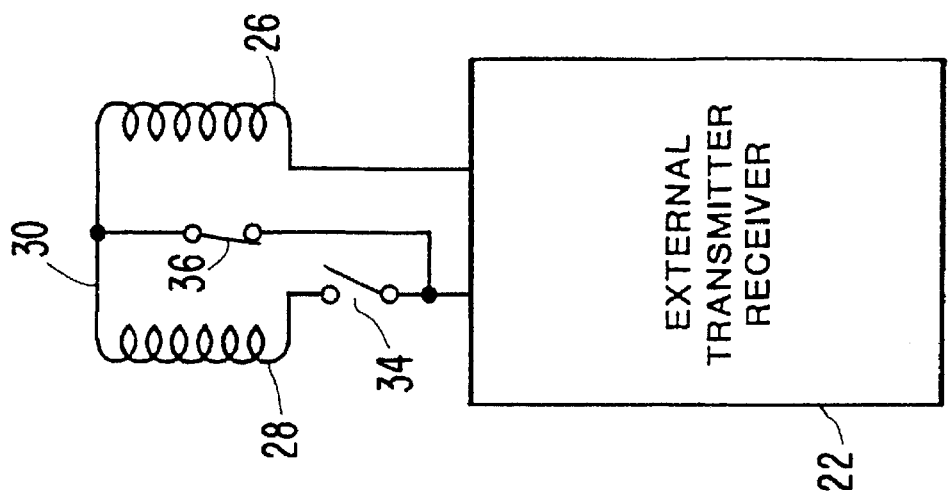
FIG. 2a is a schematic illustration of the switching system shown in FIG. 2, when the transceiver is in the transmit mode.
Figure 2:
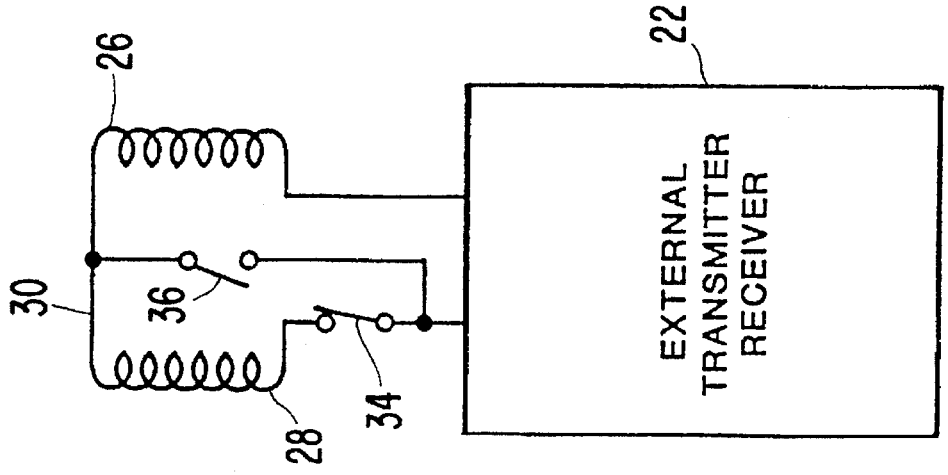
FIG. 2 is a schematic illustration of a switching system for isolating the transmit and receive modes of the transceiver of the present invention by disabling one of the coils during transmission of data from the external transceiver to the implanted device, the illustration shows the position of the switches when the transceiver is in the receive mode.

With reference now to FIGS. 2 and 2a, a relatively simple isolation technique is shown. In this embodiment, switches 34, 36 are used to disable one of the coils 28 during transmission of data from the transceiver 22 to the implanted device 10 (shown in FIG. 1). When receiving data from the implanted device 10, switch 34 is closed and switch 36 is open. This switch configuration results in having coils 26 and 28 connected in series phase opposition, thereby suppressing the effects of far-field interfering signals as described above. When in the transmission mode, however, it is desirable to disable the coil 28, which is furthest from the internal coil 16 of the implanted device 10. To disable coil 28, switch 34 is opened, while switch 36 is closed as shown in FIG. 2a. Thus, data is transmitted by coil 26 only to the internal coil 16 of the implanted device 10, thereby preventing cancellation of transmitted energy from coil 26 by coil 28.

Figure 3:
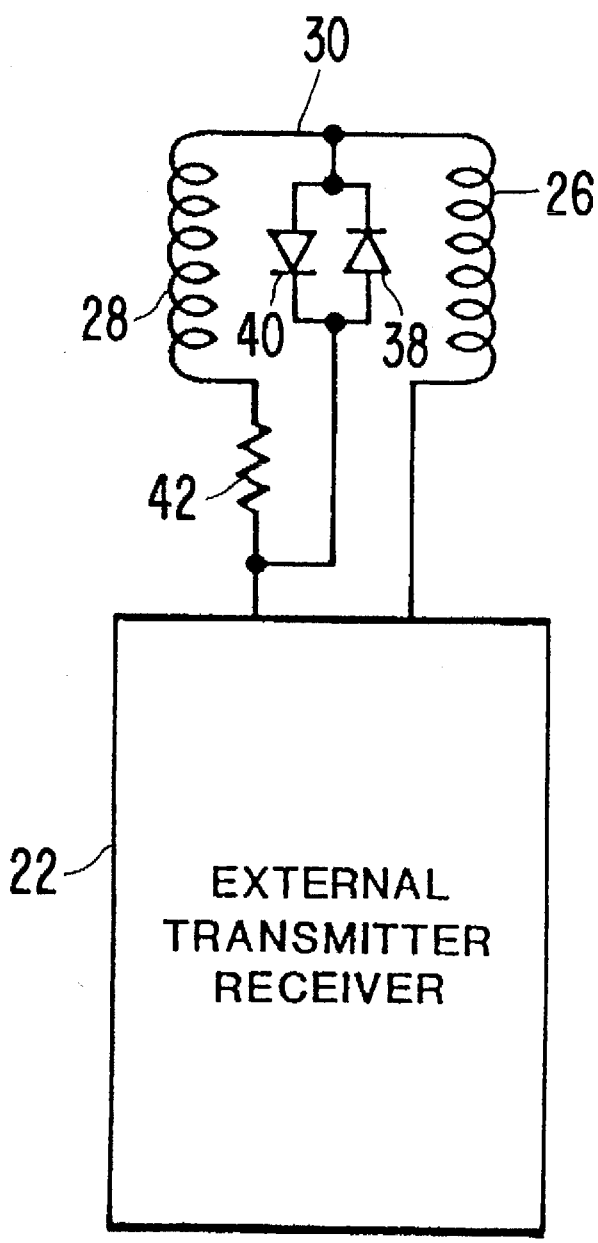
FIG. 3 is a schematic illustration of an alternative means for disabling one of the coils during transmission of data from the external transceiver to the implanted device.

An alternative isolation technique can be used if the drive voltage of the transceiver 22 is sufficiently large. As shown in FIG. 3, a pair of back-to-back diodes 38, 40 can serve to disable coil 28 during transmission. In operation, when the transceiver 22 is in receive mode, it is essentially passive, and the drive voltage is insufficient to turn on the diodes 38, 40. Therefore, in the receive mode, the coils 26, 28 operate as series-connected, phase-opposed coils that suppress the effects of far-field interference signals as described above. However, during transmission of data from the transceiver 22 to the implanted device 10, a certain drive voltage is applied to the antenna arrangement 30. If the drive voltage is sufficient to turn on the diodes 38, 40, the loop from the transmitting coil 26 back to the transceiver 22 will bypass the coil 28, thereby isolating coil 28 from the circuit during transmission of data. It should be understood that the diodes 38, 40 must be selected to prevent current from flowing therethrough when the transceiver 22 is in the receive mode, but must also have a sufficiently low activation voltage such that they isolate and disable coil 28 when the transceiver 22 is in the transmit mode. It should also be noted that if the coils 26, 28 are also tightly coupled, coil 28 may act as a shorted secondary transformer winding and potentially load-transmitting coil 26. In order to minimize this effect, a resistor 42, acting as a current-limiting resistor, may optionally be disposed between the coil 28 and the transceiver 22.

Figure 4:
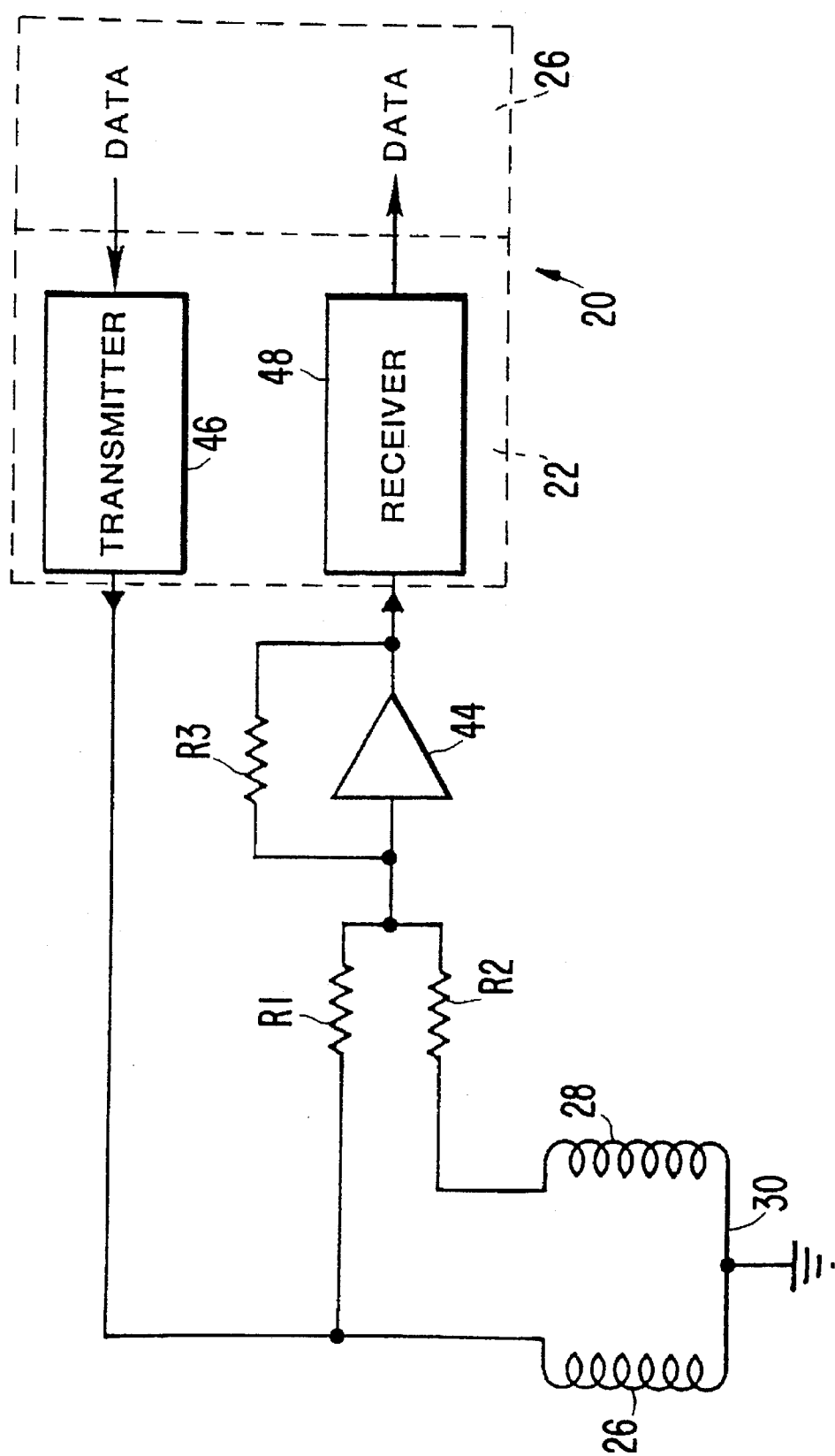
FIG. 4 is a schematic illustration of an active circuit for realizing an alternative embodiment of the present invention.

Yet another alternative manner in which to isolate the transmit and receive functions of the external device 20 is to provide an active circuit arrangement, such as that shown in FIG. 4. In the receive mode, the coils 26, 28 are connected to an operational amplifier 44, which receives signals from the series phase opposed coils 26, 28, subtracts the respective signals to suppress the far-field interference signal, and communicates the resultant value to the receiver portion 48 of the transceiver 22. The resultant value is then transmitted to the implant programmer 26 of the external device 20. When the external device 20 is in transmit mode, the transmitter portion 46 of the transceiver is connected only to the transmitting coil 26 of the coil arrangement 30, thus effectively disabling the second coil 28 from the transmitting coil 26. In this manner, the transmit power is fed to only one coil 26 to prevent transmit energy cancellation.

The above isolation techniques are exemplary, and it is to be understood that any method may be employed to isolate the transmit and receive functions of the series opposed coil arrangement 30 of the external device 20. It should also be understood that similar far-field phase cancellation techniques would also apply to antennae technology, provided that the antennae separation is small compared to the wavelength of the fields under consideration.

While this invention has been described in conjunction with specific embodiments thereof, it is evident that many alternatives, modifications and variations will be apparent to those skilled in the art. Accordingly, the preferred embodiments of the invention, as set forth herein, are intended to be illustrative, not limiting. Various changes may be made without departing from the true spirit and full scope of the invention, as defined in the following claims.

What is claimed is:

1. An electronic device for non-invasively communicating with an implanted electronic device, comprising:

a transceiver, including an antenna, a transmitter portion and a receiver portion, said transceiver including means to send data to and receive data from said implanted device; and said antenna comprising first and second coils arranged in serial phase opposition to suppress far-field interference signals when said transceiver is receiving data from said implanted device.

2. The electronic device of claim 1, further comprising an isolating circuit including means to isolate a transmit mode of said transceiver from a receive mode of said transceiver.

3. The electronic device of claim 2, wherein said isolating circuit comprises disabling circuit means for disabling said second coil when said transceiver is transmitting data to said implanted device.

4. The electronic device of claim 3, wherein said disabling circuit means comprises a switch.

5. The electronic device of claim 3, wherein said disabling circuit means comprises a pair of diodes connected between said first and second coils and operable to disable said second coil when a transceiver voltage during transmission of data exceeds a predetermined level.

6. The electronic device of claim 5, wherein said disabling circuit means further comprises a resistor disposed between said transceiver and said second coil.

7. The electronic device of claim 1, further comprising a subtracting circuit for subtracting a first signal received on said first coil and a second signal received on said second coil, said subtracting circuit comprising an operational amplifier connected between said receiver portion and said first and second coils, said operational amplifier transmitting a signal representing a resultant of a subtraction of said first and second signals to the receiver portion of said transceiver.

8. The electronic device of claim 7, wherein said transmitter portion of said transceiver is connected to only one of said first and second coils.

9. The electronic device of claim 7, wherein said first and second coils have a spatial separation in the range of 0.25 to 1.00 inch.

10. The electronic device of claim 1, wherein said first and second coils have a spatial separation in the range of 0.25 to 1.00 inch.

11. An electronic device, comprising:
a transceiver and an antenna coupled to said transceiver, said antenna comprising: a first coil and a second coil, said first and second coils being arranged in series phase opposition when said transceiver is receiving data from an implanted device, said arrangement of said first and second coils suppressing far-field interference signals.

12. The device of claim 11, further comprising an isolating circuit for isolating a transmit mode of said transceiver from a receive mode of said transceiver.

13. The device of claim 12, wherein said isolating circuit comprises disabling circuit means for disabling said second coil when said transceiver is transmitting data.

14. The device of claim 13, wherein said disabling circuit means comprises means for disabling said second coil when said transceiver is transmitting data.

15. The device of claim 13, wherein said disabling circuit means comprises diodes connected and arranged to disable said second coil when said transceiver is transmitting data.

16. The device of claim 11, wherein said first coil is operable to receive a first signal and said second coil is operable to receive a second signal, said device further comprising a substraction circuit operable to subtract said first and second signals.

17. The device of claim 16, wherein said subtraction circuit comprises an operational amplifier connected to said first and second coils and a receiver portion of said transceiver, said operational amplifier subtracting said first and second received signals to generate a resultant signal, said resultant signal being transmitted to said receiver portion.

18. The device of claim 17, wherein said first coil and said second coil have a spatial separation in the range of 0.25 to 1.00 inch.

19. The device of claim 16, wherein said transceiver includes a transmitter portion coupled to only one of said first and second coils.

20. The device of claim 11, wherein said first coil and said second coil have a spatial separation in the range of 0.25 to 1.00 inch.

21. A method for suppressing far-field interference signals when non-invasively communicating with an implanted electronic device using an external transceiver, comprising the steps of:
receiving a signal from said implanted device via an antenna of said transceiver, said antenna comprising a first coil and a second coil, said first and second coils being spatially separated and arranged in serial phase opposition;
receiving a first signal on said first coil and a second signal on said second coil;
subtracting said first signal and said second signal to obtain a resultant signal, said resultant signal representing data received from said implanted device; and
transmitting said resultant signal to a receiver portion of said transceiver.

22. The method of claim 21, further comprising:
isolating a transmit mode of said transceiver from a receive mode of said transceiver by disabling said second coil from said first coil when said transceiver is transmitting data to said implanted device.

23. The method of claim 22, wherein said step of disabling comprises:
engaging a switch to disable said second coil when said transceiver is transmitting data to said implanted device.

24. The method of claim 22, wherein said step of disabling comprises:
using a pair of diodes between said first and second coils to automatically disable said second coil when a transceiver voltage during transmission exceeds a predetermined level.

25. The method of claim 21, wherein said step of subtracting comprises:
transmitting said first signal and said second signal to an operational amplifier operable to subtract said first and second signals to obtain said resultant signal.

26. The method of claim 21, further comprising:
disabling said second coil when said transceiver is transmitting data to said implanted device by connecting a transmitter portion of said transceiver to only said first coil; and
transmitting said first signal and said second signal to an operational amplifier when said transceiver is receiving data from said implanted device, said operational amplifier being operable to subtract said first and second signals to obtain said resultant signal, and transmitting said resultant signal to said receiver portion of said transceiver.

* * * * *